United States Patent [19]

Wang et al.

[11] Patent Number: 4,524,226

[45] Date of Patent: Jun. 18, 1985

[54] PREPARATION OF NITRO COMPOUNDS BY VAPOR PHASE NITRATION OF ALDEHYDES

[75] Inventors: Shu-Chieh P. Wang, Columbia; Martin B. Sherwin, Potomac, both of Md.

[73] Assignee: W. R. Grace & Co., New York, N.Y.

[21] Appl. No.: 563,209

[22] Filed: Dec. 19, 1983

Related U.S. Application Data

[63] Continuation-in-part of Ser. No. 510,860, Jul. 5, 1983, abandoned.

[51] Int. Cl.$^3$ .............................................. C07C 79/02
[52] U.S. Cl. ..................................... 562/948; 568/947
[58] Field of Search ................ 568/927, 939, 947, 948

[56] References Cited

U.S. PATENT DOCUMENTS 2,894,041  7/1959  Berg .................................... 568/948
3,689,576  9/1972  Bachman et al. .
3,780,115  12/1973  Lhonore et al. .
3,869,253  3/1975  Lhonore et al. .
4,260,838  4/1981  Lhonore et al. .
4,313,010  1/1982  Lhonore et al. .

OTHER PUBLICATIONS

*Nitration Studies,* Bachman et al., 35, J. Org. Chem., 4229, (1970).
*Vapor Phase Nitration of Aliphatic Ethers, Alcohols, Ketones and Carboxylic Acids,* Hass et al., 76, J.A.C.S., 2692, (1954).
*Nitration of Gaseous Paraffins,* Hass et al., 28, Ind. & Eng. Chem., 339.
Urbanski, Chemistry and Technology of Explosives, vol. I, The Macmillan Co., 1964, pp. 130, 137 and 138.

Primary Examiner—Leland A. Sebastian
Attorney, Agent, or Firm—Howard J. Troffkin

[57] ABSTRACT

A process for selectively forming nitro compounds by contacting, at elevated temperature and pressure and in a homogeneous gas phase, an aldehyde having from two to ten carbon atoms with nitrogen dioxide alone or in the presence of oxygen and/or water.

18 Claims, 1 Drawing Figure

U.S. Patent    Jun. 18, 1985    4,524,226
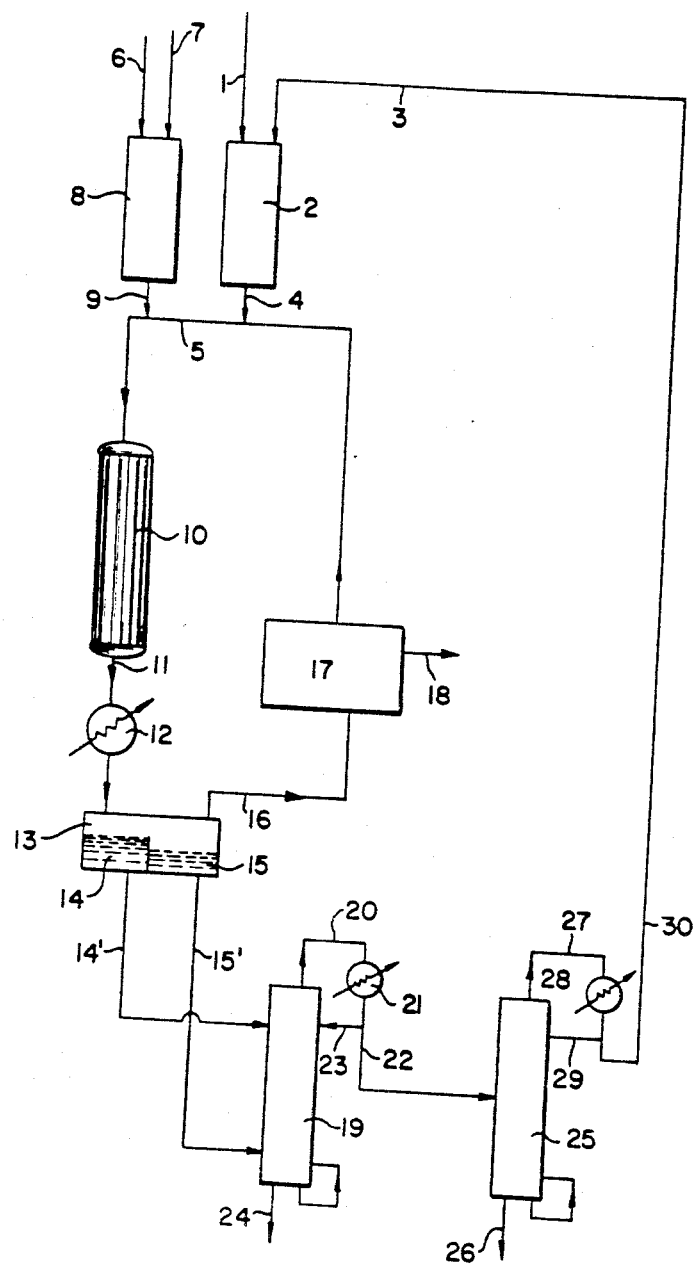

PREPARATION OF NITRO COMPOUNDS BY VAPOR PHASE NITRATION OF ALDEHYDES

This application is a continuation-in-part application of copending U.S. application Ser. No. 510,860, filed July 5, 1983, now abandoned.

BACKGROUND OF THE INVENTION

The present invention is directed to a process of forming a nitroparaffin and nitroaromatic compounds by gaseous phase reaction of an aldehyde with nitrogen dioxide. The present process provides a method to form pre-selected nitro compounds based on the particular aldehyde feed. The process further alleviates certain processing steps required in the previously used nitration of hydrocarbon feed such as ethane, propane and the like.

Processes to form nitroparaffins by gaseous phase nitration are known. U.S. Pat. Nos. 3,780,115 and 3,869,253 teach that nitration of saturated hydrocarbons higher than methane can be accomplished by contacting the hydrocarbon feed with nitrogen dioxide in the presence of oxygen, such as in the form of air. The reactant gases are preheated and then introduced into the reaction zone where the gaseous phase nitration is carried out at elevated pressure and at elevated temperature. The gaseous effluent emitted from the nitration reaction zone is rapidly quenched. The quenched mixture then enters a separator where the gaseous materials in the form of unreacted hydrocarbon, nitric oxide, carbon monoxide and carbon dioxide are removed for subsequent purification and recycling and the remaining phase liquid materials are separated by decantation and the nitroparaffins are recovered by distillation. This nitration process yields a mixture of products having a predominance of nitropropane and nitroethane.

French Publication 78/32,118 discloses that the nitroparaffins product mixture can be made to have an increased yield of nitromethane, the most commercially desired product, by utilizing ethane as the hydrocarbon feed in the homogeneous gas phase nitration. The nitration process can be further enhanced by recycling into the hydrocarbon feed some of the nitropropane product and/or by conducting the nitration in the presence of an inert gas such as nitrogen, hydrogen or argon.

U.S. Pat. No. 4,260,838, similar to the above French reference, teaches that the gas phase nitration process of U.S. Pat. Nos. 3,780,115 and 3,869,253 can be improved by altering the feed stock to obtain suitable percentages of different nitroparaffins as suits the needs of the marketplace. This patent teaches that the feed stock be made up of a mixture containing propane, preferably recycled nitroparaffin and possibly inert gas and/or another alkane. The nitrating agent can be either nitrogen dioxide or nitric acid.

Each of the conventional processes, such as those in the above referenced patents, relies on the use of a hydrocarbon feed which provides a nitroparaffin product mixture. These processes have the further defect of providing low yield of nitroparaffin mixture and low selectivity of the most commercially desired compound, nitromethane. Finally, because of the low yield, processes which are based on the gaseous phase nitration of saturated hydrocarbons produce a large volume of gaseous reaction effluents composed predominantly of unreacted hydrocarbon. In order to enhance these prior art processes, the unreacted hydrocarbons must be separated and recovered from the remaining gases, such as by cryogenic means, and then recycled as part of the process feed. Such separation and recovery required additional equipment and adds to the processing costs of the known processes.

A method to selectively form particular nitroalkanes or nitroaromatics from easily available and processable feed is highly desired. It is particularly desired to have a process to selectively form nitromethane, a very industrially useful product.

SUMMARY OF THE INVENTION

An object of the present invention is to provide a process by which a selective nitroparaffin can be formed or that a selective nitro compound is the predominant compound of the resultant products.

Another object of the present invention is to provide a process by which the various unreacted feed materials are readily separated and recyclable.

Another object of the present invention is to provide a process by which one can selectively form nitromethane from readily available and processable materials.

The process of the present invention is capable of selectively forming particular nitrohydrocarbon compounds by contacting at elevated temperature and pressure in a homogeneous gas phase a $C_2$ to $C_{10}$ aldehyde with nitrogen dioxide, preferably in the presence of oxygen and/or water.

DETAILED DESCRIPTION OF INVENTION

A process for selectively forming particular aromatic or aliphatic nitro compounds comprises contacting under homogeneous gas phase reaction conditions an aldehyde with nitrogen dioxide, preferably in the presence of oxygen and/or water.

The prpcess of homogeneous nitration is generally performed by initially preheating the reactants before they are carried into the reaction zone. The preheating conditions are preferably substantially the same temperature and pressure as the reaction conditions, as fully described below.

The reactant feed of the present process can be selected from aliphatic or aliphatic-aromatic aldehyde compounds or mixture thereof. The term "aldehyde" as used in the present disclosure and in the claims appended hereto refers to compounds having at least one carboxyl oxygen atom covalently bonded to a carbon atom, having from two to ten, preferably two to five carbon atoms for aliphatic compounds or seven to ten, preferably seven to eight carbon atoms for aromatic ring containing compounds, and having the carbon atom which is bonded to the oxygen be further bonded only to hydrogen and carbon atoms. The preferred aldehydes are aliphatic aldehydes. In view of nitromethane being the most commercially important product, the most preferred compound is acetaldehyde.

The particular structure of the aldehyde used as the feed in the subject process will be the determinative element as to what nitro compound is to be formed or what predominant nitro compound is to be formed from a mixture. For example, when the aldehyde is represented by

in which R represents an alkyl, alkaryl or aryl, RNO$_2$ will be the sole or dominant product formed. The most preferred aldehyde is represented when R is methyl.

Examples of aldehydes which are useful as a feed in the subject process are acetaldehyde, propionaldehyde, butyraldehyde and the like. The specific compound will be dictated by the desired nitro compound and the economics and availability of the aldehyde feed.

The aldehyde compounds useful in the present process preferably do not contain non-hydrocarbon groups except for the carboxyl oxygen, as described above. However, the compounds may contain non-hydrocarbon groups which will not inhibit the subject process, such as nitriles and the like. The supply of aldehydes may also contain small amounts of other compounds, such as lower or higher homologs of the aldehyde described above and/or other oxygen atom containing compounds without interferring with the presently obtained unexpected result.

The above described aldehydes are contacted in the reaction zone with nitrogen dioxide. The nitrogen dioxide, per se, or presursors (such as N$_2$O$_4$ or HNO$_3$) capable of forming and providing NO$_2$ under reaction zone conditions are feed materials readily obtainable commercially. The terms "nitrogen dioxide","nitrogen peroxide" or "NO$_2$" as used in this disclosure and in the appended claims shall each refer to the compound NO$_2$ or its precursors except when used to describe the reactant in the reaction zone wherein the terms shall each refer to the compound NO$_2$, per se.

It is preferred that the feed also includes oxygen, usually in the form of air. The oxygen as well as the nitrogen dioxide can be at least partially obtained from recycled unreacted materials which have been separated and purified by conventional methods from the reaction product as more fully described below.

The feed may further contain inert gas such as nitrogen, carbon monoxide, carbon dioxide, argon or mixtures thereof. Further, the feed can contain water either as part of the carrier for the aldehyde reactant feed or as a part of the nitrating agent.

The conditions and parameter ranges for conducting the homogeneous gaseous nitration of aldehydes are (a) that the reaction zone feed be in a molar ratio of NO$_2$ or equivalent to aldehyde of from about 0.3 to 4 or greater and preferably from about 0.5 to 3. The environment can be, therefore, either a reducing or an oxidizing environment depending on the feed ratio used. When oxygen is used as an additional feed, it should be in from about 0.05 to 1 mole per mole of NO$_2$ or equivalent. The reaction is carried out at elevated temperature of from about 100° to about 500° C. and preferably from 150° to 400° C. The reaction is carried out under elevated pressure of from about 5 to 20 bars with from 5 to 12 bars being preferred. The combined temperature and pressure conditions must be such as to maintain the reactants in a homogeneous gas phase.

It has been found that by causing the homogeneous gaseous nitration to occur under the combined elevated temperature and high pressure conditions stated herein one attains a high yield of nitrocompounds with very high selectivity to a specific nitrocompound, RNO$_2$ as described above. These achievements are highly desired and attainable only under the present reaction conditions.

The inert gases in the feed (A, CO, CO$_2$, N$_2$) can be from about 0 to 90 volume percent. The water can be present in from about 0 to 30 weight percent based on the NO$_2$ with at most 10 weight percent being preferred. The reaction contact time of the reaction gases in the reaction zone can be from about 0.5 to 20 seconds with the order of from about 1 to 12 seconds being preferred.

Referring to the drawing to illustrate the subject process, an aldehyde such as acetaldehyde, etc. is transported from a reservoir (not shown) by pipeline 1 to preheater 2. Preheater 2 is also used to preheat the aldehyde being recirculated through pipeline 3, as more fully described hereinbelow. The preheater is maintained at substantially the reaction zone entry temperature of about 100° to 500° C. and pressure of from about 5 to 20 bars. The preheated aldehyde is then passed through pipeline 4 to reactor intake pipeline 5. The nitrogen dioxide and the oxygen (as air, when used) are introduced to preheater 8 via pipelines 6 and 7, respectively. The preheater 8 is maintained at temperature and pressure conditions substantially the same as that of preheater 2. The mixed preheated NO$_2$/O$_2$ gases pass through pipeline 9 to reactor intake pipeline 5 using gas-gas mixing devices such as spargers, venturis, etc. The preheated gases are passed through reactor 10 which may be in the form of a tubular reactor heated by salt at a temperature of from 100° to 500° C., preferably from 150° to 400° C. and at a pressure of approximately 5 to 20, preferably about 5 to 12 bars. The reactor effluents withdrawn through pipeline 11 are cooled to ambient temperature in cooler 12 which uses super-cooled water to rapidly cool the gases. The cooled reactor effluents are separated in the separator 13. The liquid effluent separates into organic liquid phase 14 and aqeuous liquid phase 15.

The uncondensed gaseous reaction effluents are removed from the separator 13 through pipeline 16. The uncondensed gaseous reaction effluents obtained in the present process are generally a mixture of components composed predominantly of nitrogen monoxide and inert gases. These effluent gases are distinctly different from those encountered in conventional hydrocarbon gaseous nitration processes where the effluent gases are rich in unreacted hydrocarbons. In such conventional processes the unreacted hydrocarbons must be separated from the NO (which must be separately treated) and recycled as part of the feed. Such separation is complex and costly. In contrast, the present uncondensed effluent gases of separator 13 are substantially free of unreacted aldehyde and thereby do not require separation. Instead, these gases can be directly treated at station 17 to re-oxidize the nitrogen oxide to nitrogen dioxide for reuse by, for example, directly injecting oxygen into the gaseous effluent. To prevent build-up of inert gases due to the recycling of gaseous effluent, a purge stream 18 is maintained.

The condensed organic and aqueous liquid phases 14 and 15, respectively, are removed from separator 13 and sent by pipelines 14' and 15' to an azeotropic distillation column 19. When the nitro compound product has a lower density than water (i.e. some C$_4$ and higher nitro compounds) the organic and aqueous liquid phases 14 and 15 will be in reversed position in separator 13 to that shown. In such instances (not shown) line 14' will enter the bottom portion of column 19 and line 15' will enter the top portion of column 19. Azeotropic distillation column 19 normally operates at a pressure of about 1.25 bars or less and at temperatures sufficient to azeotropically distill the nitroalkane or nitroaromatic products as well as other compounds having a boiling point lower than the nitro products, including any unreacted aldehyde feed with associative water. These materials are passed via pipeline 20, condenser 21 and pipeline 22 to distillation column 25. Some of the distillate may be recycled to the azeotropic column 19 by pipeline 23. The majority of the water and the heavy by-products such as acids and the like are removed as bottom products through pipeline 24. This stream containing heavy by-products may be recycled to reactor 10 via line 3.

The distillation column 25 operates at a pressure of about 1.25 bars or less and at a temperature range sufficient to remove overhead any unreacted aldehyde as well as any other oxygenated hydrocarbon by-product, such as a temperature range of from 30° C. to 95° C. The bottom product of column 25 is removed by pipeline 26 and is composed of a mixture of a major amount of nitroalkanes or mixture of nitroalkanes or nitroaromatic as is appropriate based on the aldehyde feed used. In addition there may be present a small amount of water (from the prior azeotropic distillation) and trace amounts of oxygenated hydrocarbon by-products. The material removed by pipeline 26 is subsequently chemically treated (not shown) to remove any trace contaminants then fed to a dehydration column (not shown) and where a mixture of nitrocompounds are produced to a fractionation column (not shown) to recover pure nitro products. The nitro product of the present process is either composed of a single nitro compound such as nitromethane or of a mixture of nitro compounds highly selective with respect to one nitro product which is dependent on the starting aldehyde feed.

The overhead effluent of column 25 is removed by pipeline 27 through condenser 28. Some of the distillate may be recycled to column 25 by pipeline 29. The overhead distillate is made up predominantly of aldehyde with small amounts of other oxygenated hydrocarbons such as acids, which can be readily recycled via pipeline 30 to preheater 2 as part of the feed.

By utilizing an aldehyde as the feed material in the subject process it has been unexpectedly found that one can readily form nitroalkane or nitroaromatic compounds, that the nitro compound product will be highly selective based on the particular aldehyde used as the feed and that the unreacted aldehyde can be readily separated and recycled as part of the feed to further improve the effectiveness and efficiency of the subject process The subject process provides a means of custom directing the formation of a preselected nitro compound.

The following examples are given for illustrative purposes only and are not meant to be a limitation on the claims appended hereto. All parts and percentages are by weight unless otherwise indicated.

EXAMPLE I

A series of production runs were conducted using acetaldehyde as the feed. Each feed material was preheated to 150° C. at 10 bars. The nitrogen dioxide and oxygen (when used) were preheated separately from the acetaldehyde and water (when used). The preheated feed materials were then mixed and reacted in a tubular reactor for a residence time of 8 seconds. The reactor effluent was quenched. The nitric oxide, carbon monoxide and carbon dioxide were removed and the nitric oxide treated with oxygen to obtain nitrogen dioxide which was recycled to the reactor. The remaining liquid was distilled to azeotropically remove the nitro compound and low boiling oxygenated hydrocarbon including unreacted acetaldehyde. The azeotropic distillate was further distilled to separate the nitro compound from the oxygenates. The nitro compound was nitromethane. No other nitro compound was detected.

EXAMPLE II

A series of production runs were conducted in the same manner as in Example I above except that the reaction conditions were varied. Details of the runs are given in Table I below:

TABLE I

| Run No. | 1 | 2 | 3 | 4 |
|---|---|---|---|---|
| Temperature (°C.) | 150 | 190 | 190 | 250 |
| Pressure (atm) | 7.8 | 10.5 | 7.8 | 10.2 |
| Feed (mmoles/hr) | | | | |
| Acetaldehyde | 2020 | 2263 | 2240 | 2265 |
| Nitrogen Dioxide | 1032 | 1198 | 1486 | 1311 |
| Water | 1925 | 1889 | 1886 | 1759 |
| Oxygen | 433 | 303 | 303 | 303 |
| Nitrogen | 4685 | 6587 | 6587 | 6587 |
| $NO_2/CH_3CHO$ | 0.51 | 0.53 | 0.66 | 0.57 |
| Acetaldehyde Conversion (%) | 23.8 | 27.5 | 28.4 | 40.5 |
| Nitromethane Yield, %* | 21.0 | 25.5 | 24.6 | 23.0 |

*moles of nitromethane/total moles of $C_1$ compounds produced

While the invention has been described in connection with certain preferred embodiments, it is not intended to limit the invention to the particular form set forth, but, on the contrary, it is intended to cover such alternatives, modifications and equivalents as defined by the appended claims.

What is claimed is:

1. A process for selectively forming nitroalkanes comprising contacting in a reaction zone in a homogeneous gas phase and at an elevated pressure of from about 5 to about 20 bars, a temperature of from about 100° C. to about 500° C. and a time of from about 0.5 to 20 seconds at least one $C_2$–$C_{10}$ aliphatic aldehyde with nitrogen dioxide and recovering the formed nitroalkane compound.

2. The process of claim 1 wherein the reaction zone further contains oxygen, water or both.

3. The process of claim 1 wherein the aldehyde is selected from a $C_2$ to $C_5$ aliphatic aldehyde or mixtures thereof.

4. The process of claim 2 wherein the aldehyde is selected from a $C_2$ to $C_5$ aliphatic aldehyde or mixtures thereof.

5. The process of claim 2 wherein the aldehyde is acetaldehyde.

6. The process of claim 3 wherein the aldehyde is acetaldehyde.

7. The process of claim 1 wherein the process further comprises cooling the reaction zone effluent, separating the resulting liquid phase effluent from the non-condensed gaseous effluent and recovering any aldehyde therefrom and returning at least a portion of said aldehyde to the reaction zone.

8. The process of claim 2 wherein the process further comprises cooling the reaction zone effluent, separating the resulting liquid phase effluent from the non-condensed gaseous effluent and recovering any aldehyde therefrom and returning at least a portion of said aldehyde to the reaction zone.

9. The process of claim 3 wherein the process further comprises cooling the reaction zone effluent, separating the resulting liquid phase effluent from the non-condensed gaseous effluent and recovering any aldehyde therefrom and returning at least a portion of said aldehyde to the reaction zone.

10. The process of claim 4 wherein the process further comprises cooling the reaction zone effluent, separating the resulting liquid phase effluent from the non-condensed gaseous effluent and recovering any aldehyde therefrom and returning at least a portion of said aldehyde to the reaction zone.

11. The process of claim 5 wherein the process further comprises cooling the reaction zone effluent, separating the resulting liquid phase effluent from the non-condensed gaseous effluent and recovering any aldehyde therefrom and returning at least a portion of said aldehyde to the reaction zone.

12. The process of claim 8 wherein the process further comprises cooling the reaction zone effluent, separating the resulting liquid phase effluent from the non-condensed gaseous effluent and recovering any aldehyde therefrom and returning at least a portion of said aldehyde to the reaction zone.

13. The process of claim 2 wherein the reaction zone pressure is from about 5 to 12 bars, temperature is from about 150°–400° C., the $O_2$ to $NO_2$ molar ratio is from about 0.05 to 1 and the $NO_2$ to aldehyde molar ratio is from about 0.3 to 3.

14. The process of claim 4 wherein the reaction zone pressure is from about 5 to 12 bars, temperature is from about 150°–400° C., the $O_2$ to $NO_2$ molar ratio is from about 0.05 to 1 and the $NO_2$ to aldehyde molar ratio is from about 0.3 to 3.

15. the process of claim 7 wherein the reaction zone pressure is from about 5 to 12 bars, temperature is from about 150°–400° C., the $O_2$ to $NO_2$ molar ratio is from about 0.05 to 1 and the $NO_2$ to aldehyde molar ratio is from about 0.3 to 3.

16. The process of claim 8 wherein the reaction zone pressure is from about 5 to 12 bars, temperature is from about 150°–400° C., the $O_2$ to $NO_2$ molar ratio is from about 0.05 to 1 and the $NO_2$ to aldehyde molar ratio is from about 0.3 to 3.

17. The process of claim 10 wherein the reaction zone pressure is from about 5 to 12 bars, temperature is from about 150°–400° C., the $O_2$ to $NO_2$ molar ratio is from about 0.05 to 1 and the $NO_2$ to aldehyde molar ratio is from about 0.3 to 3.

18. The process of claim 11 wherein the reaction zone pressure is from about 5 to 12 bars, temperature is from about 150°–400° C., the $O_2$ to $NO_2$ molar ratio is from about 0.05 to 1 and the $NO_2$ to aldehyde molar ratio is from about 0.3 to 3.

* * * * *

UNITED STATES PATENT AND TRADEMARK OFFICE
CERTIFICATE OF CORRECTION

PATENT NO. : 4,524,226
DATED : June 18, 1985
INVENTOR(S) : Shu-Chieh P. Wang and Martin B. Sherwin It is certified that error appears in the above-identified patent and that said Letters Patent is hereby corrected as shown below:

In Claim 12, line 1, delete "8" and insert --6--.

In Claim 15, line 1, delete "the" and insert --The--.

Signed and Sealed this

Twenty-second Day of October 1985

[SEAL]

Attest:

DONALD J. QUIGG

Attesting Officer

Commissioner of Patents and
Trademarks—Designate